United States Patent
Trieu

(10) Patent No.: US 7,749,268 B2
(45) Date of Patent: Jul. 6, 2010

(54) METHODS FOR TREATING THE SPINE

(75) Inventor: Hai H. Trieu, Cordova, TN (US)

(73) Assignee: Warsaw Orthopedic, Inc.

( * ) Notice: Subject to any disclaimer, the term of this patent is extended or adjusted under 35 U.S.C. 154(b) by 1006 days.

(21) Appl. No.: 10/854,458

(22) Filed: May 26, 2004

(65) Prior Publication Data

US 2005/0267577 A1    Dec. 1, 2005

(51) Int. Cl.
A61F 2/44    (2006.01)
(52) U.S. Cl. .................................... 623/17.11
(58) Field of Classification Search ............... 606/61; 623/17.11–17.16
See application file for complete search history.

(56) References Cited

U.S. PATENT DOCUMENTS

| | | |
|---|---|---|
| 4,294,753 A | 10/1981 | Urist |
| 4,877,864 A | 10/1989 | Wang et al. |
| 5,013,649 A | 5/1991 | Wang et al. |
| 5,106,748 A | 4/1992 | Wozney et al. |
| 5,108,753 A | 4/1992 | Kuberasampath et al. |
| 5,108,922 A | 4/1992 | Wang et al. |
| 5,116,738 A | 5/1992 | Wang et al. |
| 5,187,076 A | 2/1993 | Wozney et al. |
| 5,306,307 A * | 4/1994 | Senter et al. ............. 623/17.16 |
| 5,366,875 A | 11/1994 | Wozney et al. |
| 5,405,390 A | 4/1995 | O'Leary et al. |
| 5,549,679 A * | 8/1996 | Kuslich ................... 623/17.12 |
| 5,741,261 A | 4/1998 | Moskovitz |
| 5,764,844 A | 6/1998 | Mendes |
| 5,885,292 A | 3/1999 | Moskovitz |
| 6,273,916 B1 * | 8/2001 | Murphy .................... 623/23.62 |
| 6,333,312 B1 | 12/2001 | Kuberasampath |
| 6,348,055 B1 | 2/2002 | Preissman |
| 6,375,659 B1 | 4/2002 | Erbe et al. |
| 6,558,386 B1 * | 5/2003 | Cragg ........................ 606/279 |
| 6,582,439 B1 | 6/2003 | Sproul |
| 6,599,520 B2 * | 7/2003 | Scarborough et al. ....... 424/426 |
| 6,602,254 B2 | 8/2003 | Gertzbein et al. |
| 6,620,196 B1 | 9/2003 | Trieu |
| 7,090,668 B1 * | 8/2006 | U et al. ..................... 604/892.1 |
| 7,163,560 B2 * | 1/2007 | Mason ..................... 623/17.16 |
| 2001/0008980 A1 * | 7/2001 | Gresser et al. ........... 623/17.11 |
| 2002/0068974 A1 * | 6/2002 | Kuslich et al. ........... 623/17.11 |

(Continued)

FOREIGN PATENT DOCUMENTS

WO    WO93/00432    1/1993

(Continued)

OTHER PUBLICATIONS

Spine: Have Emerging Technologies Altered Outcomes; Edward N. Hanley, Jr., MD, Charlotte, NC.

(Continued)

*Primary Examiner*—Thomas C Barrett
*Assistant Examiner*—Nicholas Woodall

(57) ABSTRACT

Described are methods for therapeutically treating the spine that involve the implantation of a medical device, such as a fusion cage, disc nucleus implant, or artificial disc, that transmits loads to a volume of bone tissue of the spine, and the reinforcement of that volume of bone tissue to decrease the risk of fracture or other injury resultant of the transmitted loads.

14 Claims, 7 Drawing Sheets

U.S. PATENT DOCUMENTS

| | | | | |
|---|---|---|---|---|
| 2002/0147497 | A1* | 10/2002 | Belef et al. | 623/17.12 |
| 2003/0050702 | A1* | 3/2003 | Berger | 623/17.12 |
| 2004/0034428 | A1 | 2/2004 | McKay | |
| 2004/0193274 | A1 | 9/2004 | Trieu | |
| 2004/0215344 | A1* | 10/2004 | Hochschuler et al. | 623/17.12 |
| 2005/0055096 | A1* | 3/2005 | Serhan et al. | 623/17.11 |
| 2005/0154460 | A1* | 7/2005 | Yundt | 623/17.11 |
| 2005/0244451 | A1* | 11/2005 | Diaz et al. | 424/423 |
| 2006/0079905 | A1* | 4/2006 | Beyar et al. | 606/76 |

FOREIGN PATENT DOCUMENTS

| | | |
|---|---|---|
| WO | WO94/26892 | 11/1994 |
| WO | WO94/26893 | 11/1994 |
| WO | WO99/06563 | 2/1999 |
| WO | WO03/024316 | 3/2003 |

OTHER PUBLICATIONS

Percutaneous Vertebroplasty; Jashvant Patel, MD.

Eur Spine J Dec. 9, 2000; Wuisman Pi; Van Dijk M; Staal H; Van Royen BJ. Dept. of Orthopaedic Surgery, Free University Teaching Hospital, Amsterdam, The Netherlands.

Eur Spine J Aug. 12, 2003; Baroud G; Nemes J; Heini P; Steffen T. Orthopaedic Research Laboratory, Division of Orthopaedic Surgery, McGill University, Royal Victoria Hospital, Rm L4.65, 687 Pine Ave. West, H3A 1A1, Montreal Quebec Canada.

The Role of Vertebroplasty in Metastatic Spinal Disease; Julie G. Pilitsis M.D., Setti S. Rengachary, M.D., Dept. of Neurological Surgery, Wayne State Univ., Detroit, MI.

* cited by examiner

METHODS FOR TREATING THE SPINE

BACKGROUND OF THE INVENTION

The present invention resides generally in the field of medical devices and methods, and particularly to methods that can be used in the implantation of medical devices in the spine to treat a variety of conditions.

As further background, much of the population will experience back pain at some point. There are many causes for back pain, and many treatments for alleviating the pain. Seven cervical, twelve thoracic, and five lumbar vertebrae are included in the normal human spine. Intervertebral discs reside between adjacent vertebrae except for in the first articulation between the first two cervical vertebrae. A disc also lies between the last lumbar vertebrae and the sacrum. Diseases or disorders in any of these or other areas of the spine can cause debilitating pain as well as limited mobility in a patient.

In one field of therapy, medical devices are implanted in the spine at one or more locations to treat the spinal condition. A variety of medical devices are utilized, serving a variety of purposes. Illustratively, fusion cages and other interbody fusion devices are positioned between vertebrae to facilitate their fusion. Such devices are commonly employed in conjunction with rods, screws, hooks, or plates that are also connected to elements of the spine. Systems are also connected to the spine in the absence of fusion devices, so as to support or realign elements such as vertebrae.

Disc nucleus implants are also known, for receipt within the interior space of a damaged or otherwise ineffectual intervertebral disc. Many such devices that have been proposed are formed of hydrogels or elastomeric polymers, for absorbing impact and other forces occurring between the vertebrae.

While there is a wide variety of spinal implant devices, most have in common the feature of transferring or imparting forces to bony tissue occurring within vertebrae of the spine. These forces may at times be deleterious to those bony tissues, particularly for example in the case of patients having diseased or damaged bony tissue in critical areas of the spine.

In light of this background, there exist needs for methods for implanting medical devices in the spine in which measures are undertaken to minimize the risk that loads imparted to bony tissue by the medical devices will cause fracture or other injury to the bony tissue. The present invention is addressed to these needs.

SUMMARY OF THE INVENTION

The present invention features, in one aspect, methods for implanting a medical device in the spine wherein bone tissue that will receive loads from the medical device is strengthened so as to reduce the risk that the bone tissue will suffer injury or damage. In certain forms, the invention provides methods for implanting a device in the spine comprising implanting the device in the spine and delivering to the load-receiving bone tissue an effective amount of an osteogenic substance to strengthen the bone tissue. Illustratively, certain aspects of the invention provide methods for fusion of adjacent vertebrae of the spine wherein an osteogenic substance is delivered into bone tissue of one or both of the adjacent vertebral bodies, for example by injection of the osteogenic substance so as to deliver the osteogenic substance to a volume of bone within the vertebral bodies. In other aspects, the implantation of a disc nucleus implant into the intervertebral disc space is accompanied by delivery of an osteogenic substance to one or both of the adjacent vertebral bodies. In still other forms of the invention, the connection of a spinal implant to a posterior, anterior, or lateral surface of a vertebral body is accompanied by the delivery of an osteogenic substance into the vertebral body in areas of bone tissue to receive loads from the device. For example, an osteogenic substance can be injected into a volume of bone tissue within a vertebral body to receive a penetrating connector such as a screw or bolt, which may in turn be connected to rods, plates, ligaments, or other devices attached to the vertebral body.

In one form of the invention, an osteogenic substance is delivered into a volume of bone tissue of a vertebra, and the bone tissue is permitted to strengthen prior to the implantation of the medical device. In another form of the invention, an osteogenic substance is delivered into the bone tissue of the vertebra during the same surgical procedure in which the medical device is implanted. In still other forms of the invention, an osteogenic substance is delivered into the bone tissue of the vertebra in a procedure that occurs separately and after the procedure in which the medical device is implanted.

In additional aspects, the invention provides methods for therapeutically treating the spine of a patient. The methods include implanting a medical device in the spine that imparts loads to a volume of bone tissue of a vertebra of the spine. A cannulated delivery device is inserted into the volume of bone tissue, and a bone-strengthening substance is delivered through the cannulated delivery device and into the volume of bone tissue. The cannulated delivery device is then withdrawn.

In still further aspects, the invention provides methods for implanting a medical device in the spine of a patient. The medical device is implanted, wherein it imparts loads indirectly to a volume of bone spaced from the medical device, and a bone-strengthening substance is delivered to the load-receiving volume of bone.

In other aspects, the invention provides surgical kits that are useful for performing methods such as those described herein. The surgical kits include a medical device for implantation in the spine, an osteogenic or other bone-strengthening substance for delivery into bone tissue of at least one vertebra, and a delivery device, such as an injection device, that is equipped to deliver the substance into the bone tissue of the vertebra.

Additional aspects as well as features and advantages of the invention will be apparent from the further description herein.

DETAILED DESCRIPTION

Figure 1:
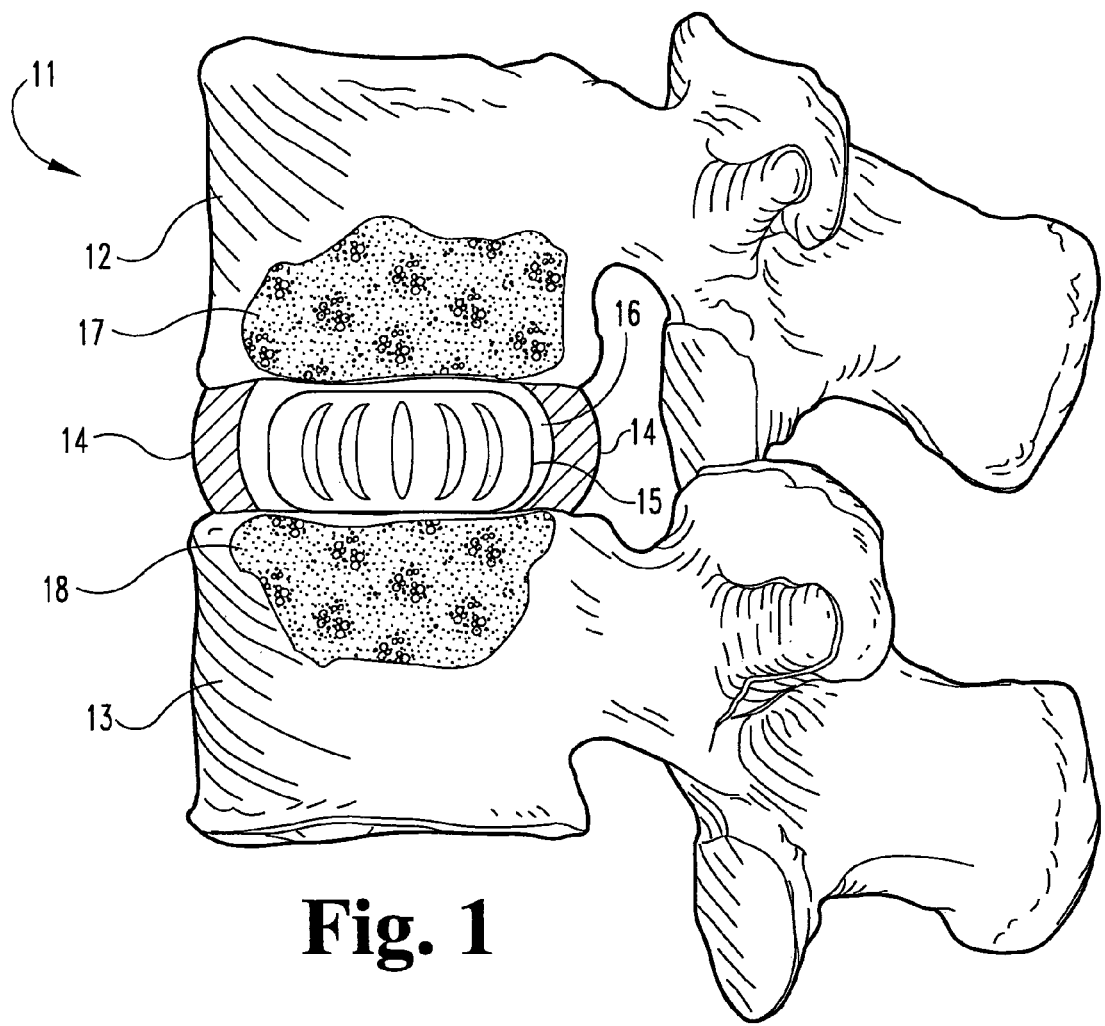
FIG. 1 provides an illustration of an intervertebral disc nucleus implant received between vertebral bodies, wherein the vertebral bodies have an interior volume of bony tissue that has been strengthened.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides, inter alia, methods for implanting a medical device in the spine wherein bone tissue of the spine that receives forces or loads from the implanted device is strengthened by the delivery of an osteogenic substance into the tissue. In this regard, the spinal vertebrae are composed primarily of a spongy or cancellous bone surrounded by a more compact, cortical bone shell. Cancellous bone is distributed as bone-plates, interconnected substantially at right angles. This is an ideal structure for supporting compressive loads but not ideal for supporting tensile, bending or torsional loads. The cortical shell of the vertebra is more dense than the cancellous bone, and is best suited to resisting bending and torsional loads. When these two types of bone are normal and healthy, the risk of fracture is minimized. However, when one or both of these types of bone are unhealthy due to systemic or localized disorders or lesions, the risk of fracture increases dramatically. As well, during the aging process, bone resorption generally increases, leading to a decrease in overall bone density and strength and an increase in the risk of fracture. The present invention addresses the risk of fracture or injury to bone tissue of the spine by the delivery of an osteogenic substance or another bone-strengthening substance to strengthen the bone tissue that will receive loads from an implanted medical device.

A wide variety of medical devices for implantation within the spine, or for replacing elements of the spine, are known. As illustrative examples, these devices include a variety of intervertebral disc implants, including for example fusion devices, disc nucleus implants, and artificial discs. Illustratively, the medical device may be a disc nucleus replacement implant adapted for receipt within the internal space of an intervertebral disc, to replace or supplement the function of the normal nucleus pulposus. Examples of such devices are described in U.S. Pat. No. 6,620,196 issued Sep. 16, 2003. Commonly, these devices include a hydrogel or an elastomeric material that absorbs compressive forces imparted by the adjacent vertebrae. Still other spinal implant devices include interbody fusion devices such as fusion cages, or other fusion implants. Such devices are implanted between vertebral bodies after removal of some or all of the intervertebral disc material. A bone growth promoting material, such as autologous or other bone pieces or a composition including an osteogenic substance, is commonly used in order to promote fusion of the two adjacent vertebrae to one another. Still other spinal implants include artificial disc implants and/or involve elements connected to lateral, anterior, and/or posterior surfaces of vertebrae, including for example screws, rods, plates, ligaments, and the like. As well, vertebral replacement devices are known, which are configured to be implanted in the place of a vertebral body that has been removed. These and other medical devices for implantation within the spine are well known to those skilled in the art, and their use is contemplated as being within the present invention.

The implantation of a medical device in the spine often transfers loads to adjacent bony tissue, sometimes exerting forces that differ from those in the normal spine. In accordance with certain aspects of the present invention, an osteogenic composition is used to strengthen a volume of bony tissue to which such loads will be applied so as to reduce the risk of fracture or other injury to the tissue caused completely or in part by the presence of the implanted medical device.

Figure 2:
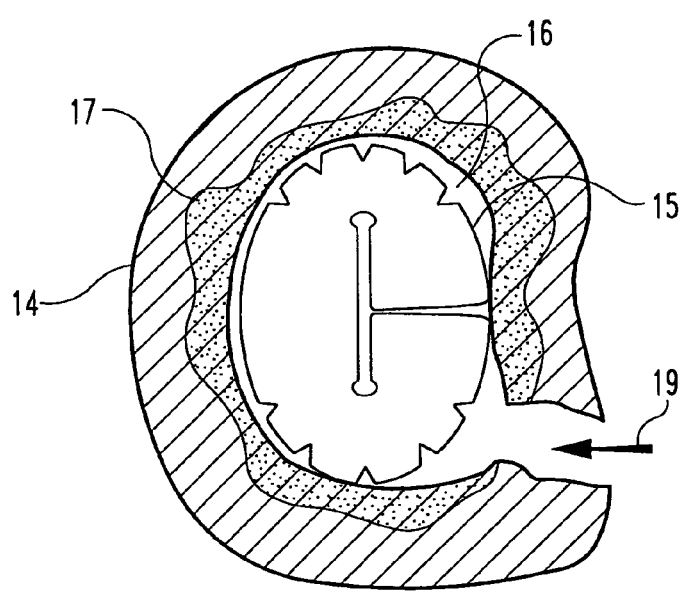
FIG. 2 provides a cross-sectional view taken through the disc space of FIG. 1.

With reference now to the Figures, several illustrative implantation scenarios that can be used in the present invention will be described. FIG. 1 provides an illustration of adjacent vertebrae in a first implant embodiment 11 of the present invention. More particularly, shown are adjacent vertebrae 12 and 13 having a relatively intact intervertebral disc annulus 14 positioned therebetween. A disc nucleus implant 15 is received within the internal disc cavity 16 bounded by the disc annulus 14. Upper vertebra 12 includes a substantial internal volume of bony tissue 17 that has been strengthened by the delivery of an osteogenic substance into the bony tissue of vertebra 12. Similarly, lower vertebra 13 has a substantial internal volume of bony tissue 18 within the vertebral body that has been strengthened by the delivery of an osteogenic substance into vertebra 13. With reference to FIG. 2, shown is a cross-sectional view taken through the intervertebral disc component shown in FIG. 1, illustrating the placement of nucleus replacement device 15 within the interior cavity 16 bounded by the disc annulus 14. Also shown for purposes of illustration is an opening 19 through which nucleus replacement device 15 was delivered into the disc space 16. In certain forms of the invention, the internal volumes of bony tissue 17 and 18 of vertebrae 12 and 13 (FIG. 1) will be dimensioned sufficiently to include a horizontal cross section encompassing at least substantially the entire surface area of the adjacent implant, as represented by phantom line 17 of FIG. 2.

Figure 3:
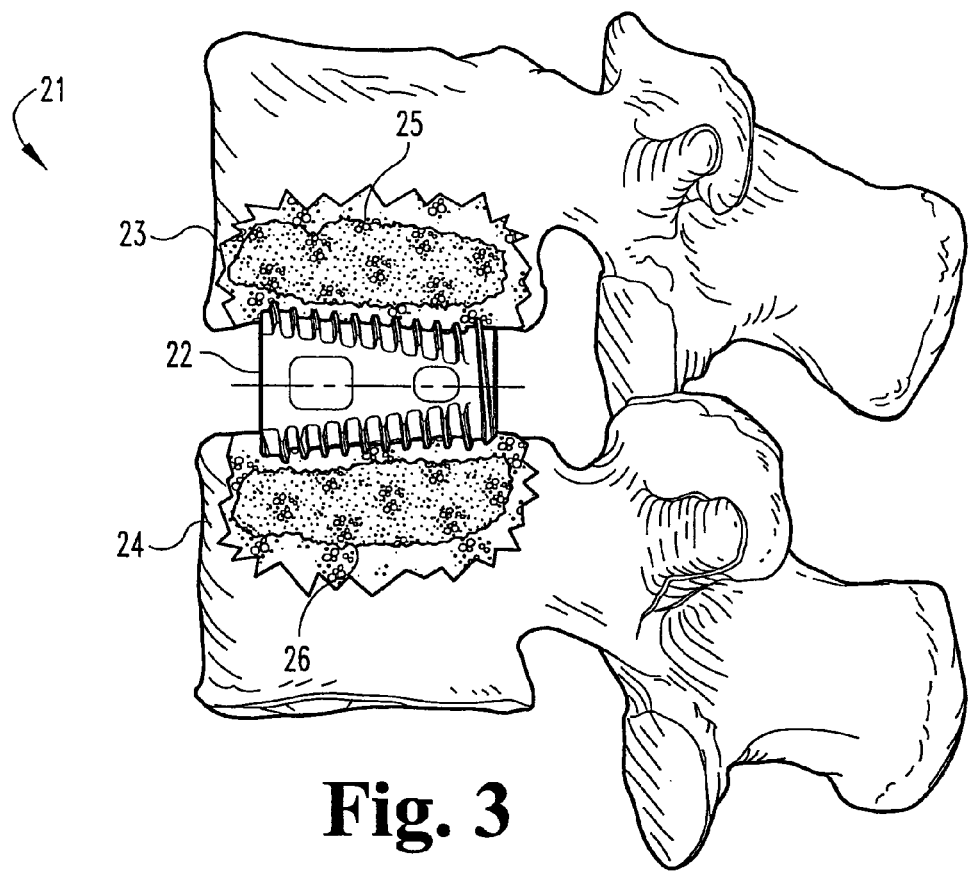
FIG. 3 provides an illustration of a spinal fusion device received between adjacent vertebral bodies, wherein the adjacent vertebral bodies include an interior volume of bone that has been strengthened.

With reference now to FIG. 3, shown is another embodiment 21 of the invention. Embodiment 21 includes at least one spinal fusion implant 22 received between adjacent vertebrae 23 and 24. Vertebra 23 includes an internal volume of bony tissue 25 that has been strengthened by delivery of an osteogenic substance and vertebra 24 includes a similar internal volume of bony tissue 26 that has been strengthened. It will be understood that with spinal fusion device 22, autogenic bone or other osteogenic substances can also be implanted within and around the device in the interbody disc space to promote fusion of the vertebrae 23 and 24.

Figure 4:
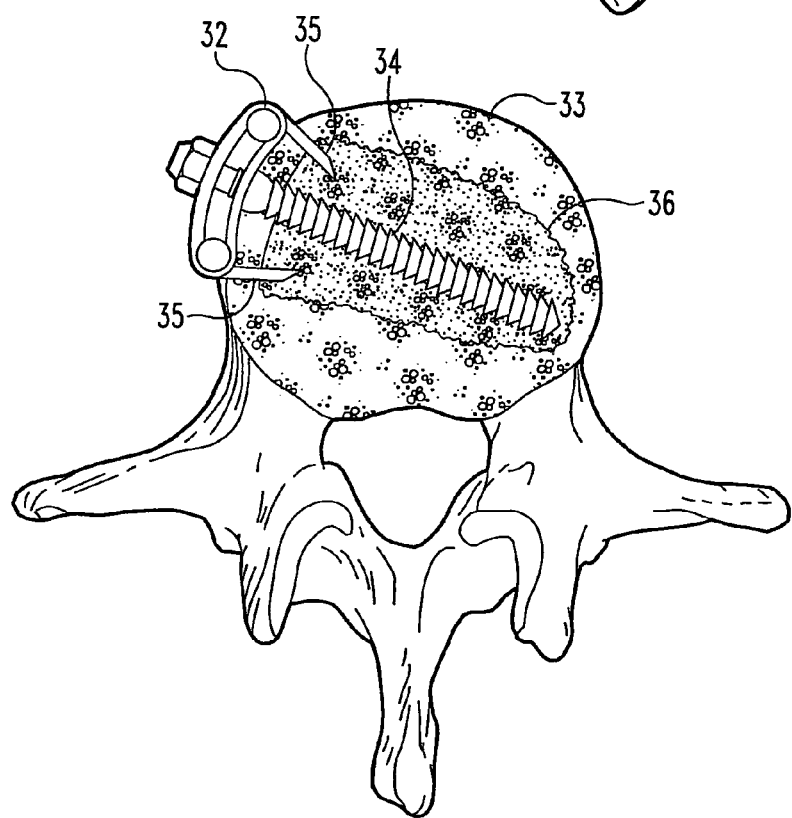
FIG. 4 provides an illustration of a spinal rod transverse connector implanted into a vertebral body, wherein an internal volume of the vertebral body has been strengthened.

Referring now to FIG. 4, shown is another embodiment 31 of the present invention. Embodiment 31 includes a spinal rod transverse connector 32 attached to an external surface of vertebra 33. Device 32 may, for example, be a transverse connector as described in U.S. Pat. No. 6,602,254 issued Aug. 5, 2003. Connector 32 is attached to vertebra 33 by a bone bolt 34 or screw as well as a number of spikes 35 projecting from the transverse connector. An internal volume of bony tissue 36 within vertebra 33 is provided, into which bone bolt 34 and spikes 35 penetrate. Volume 36 is strengthened by the delivery of an osteogenic substance, as in other embodiments described hereinabove.

Figure 5:
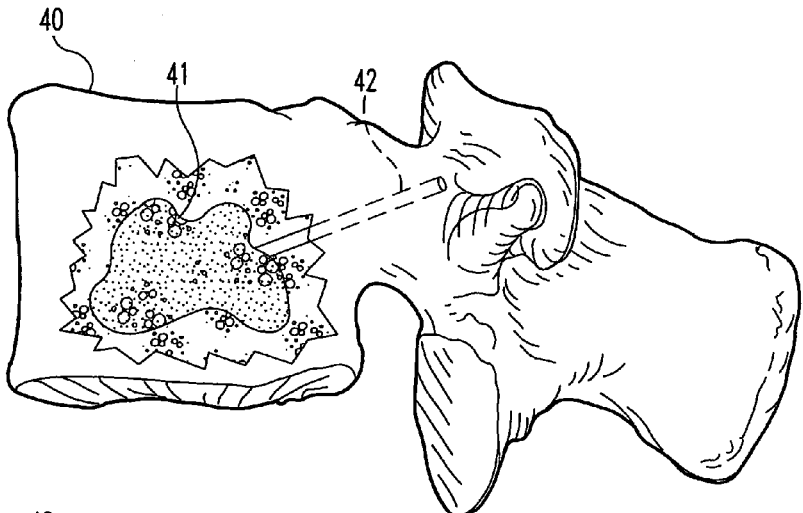
FIGS. 5-9 provide illustrations of various volumes of bone within a vertebral body that may be treated in accordance with the invention.
Figure 6:
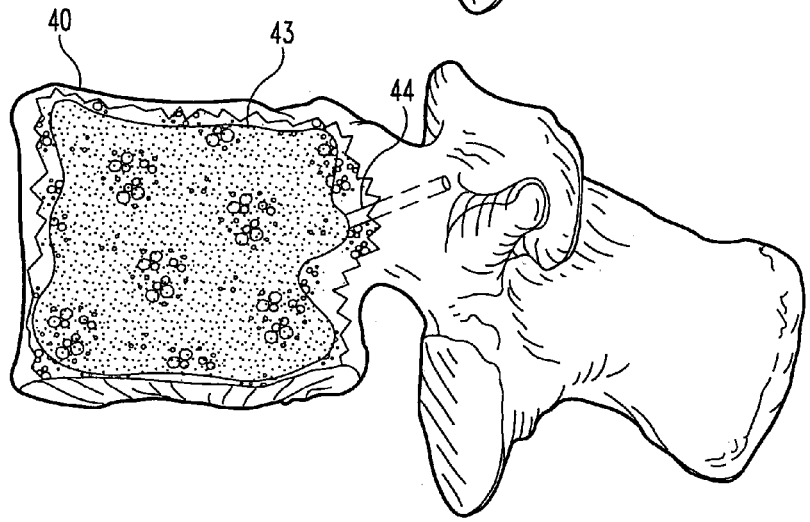

FIGS. 5 through 9 illustrate various embodiments of the invention wherein one or more internal volumes of bone within intervertebral bodies have been strengthened. Particularly, FIG. 5 illustrates an embodiment in which a central volume of bone 41 within a vertebral body 40 has been strengthened, for example by injection through access channel 42 created within the vertebrae. Access channel 42 can be provided, for example, by an intrapedical/percutaneous approach (although other approaches such as transpedicular approaches can also be used within the invention). FIG. 6 illustrates an embodiment in which an internal volume 43 of vertebral body 40 has been strengthened, wherein volume 43 constitutes substantially the entire internal volume of bone of vertebral body 40. This strengthened volume 43 can be provided via access through channel 44.

Figure 7:
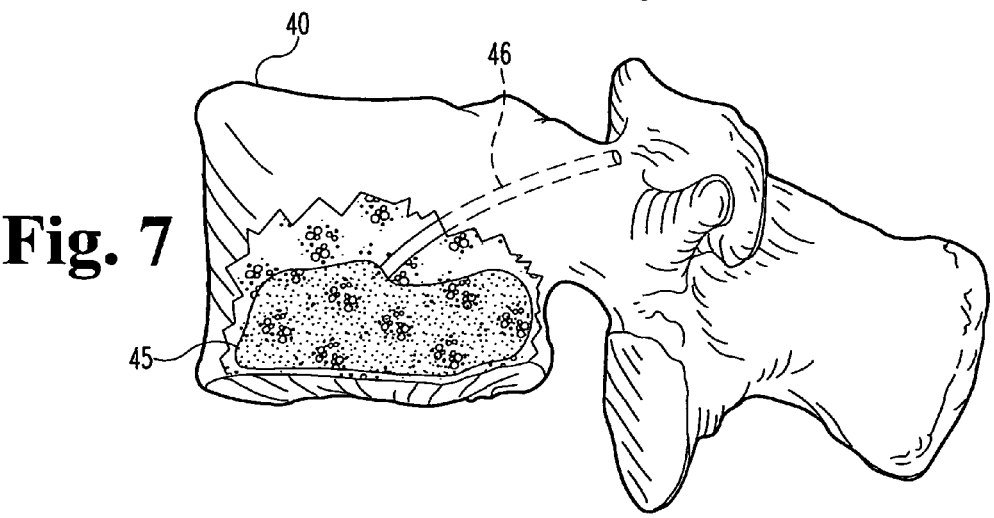
Figure 8:
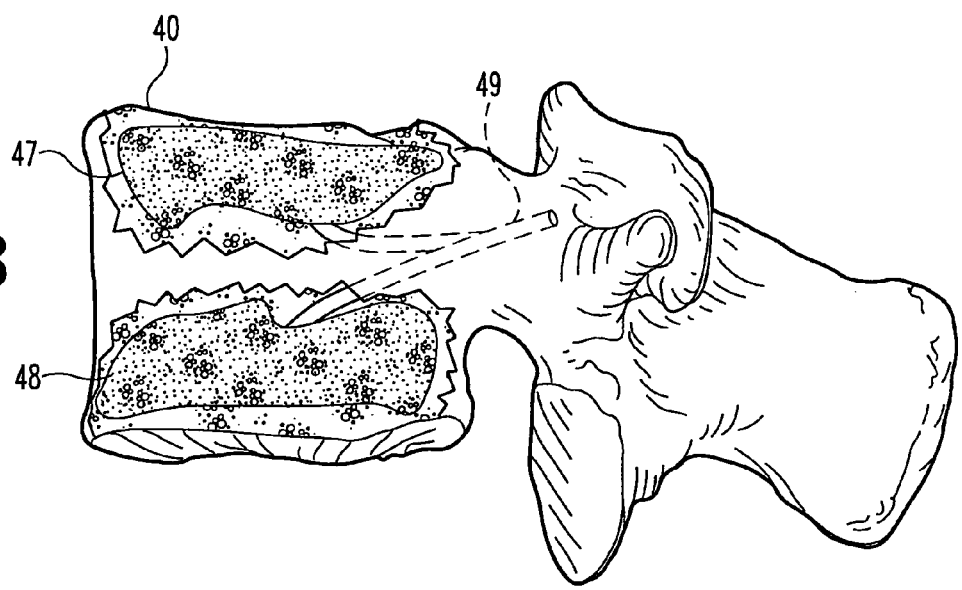
Figure 9:
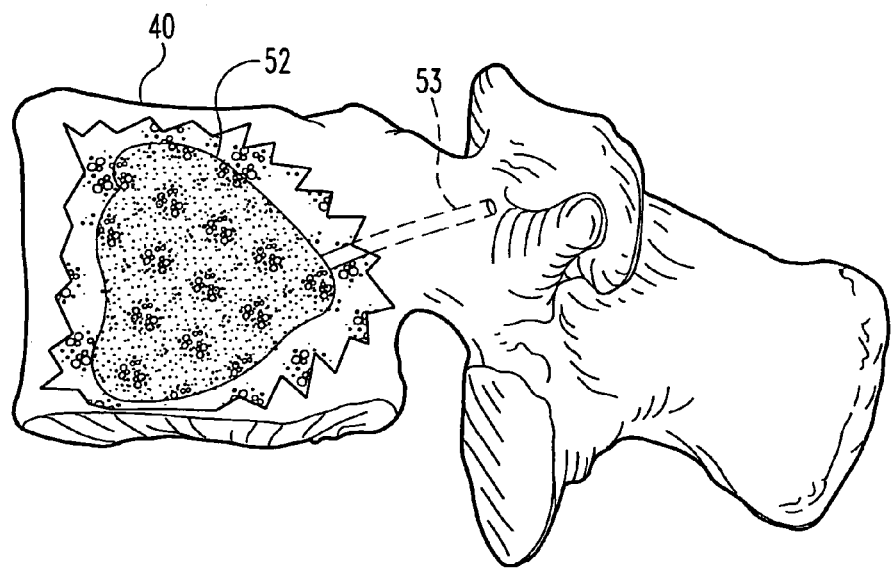

As shown in FIG. 7, the invention also contemplates the strengthening of an internal volume of bone 45 within a vertebral body 40 that generally overlies one of the endplates of vertebral body 40. As in the embodiments disclosed above, the osteogenic substance or other bone-strengthening agent can be provided via access channel 46. In a similar vein, FIG. 8 discloses an embodiment wherein internal volumes 47 and 48 have been strengthened, each overlying one of the endplates of vertebral body 40. The bone strengthening substance can be provided via access channel 49 having branches 50 and 51 diverging toward the respective endplates of vertebral body 40. Shown in FIG. 9 is an internal volume 52 of strengthened bone within vertebral body 40 provided by the delivery of a bone-strengthening substance via access channel 53. Bone volume 52 may be provided, for example, as a restoration of vertebral height in a patient in need thereof.

Each of the embodiments disclosed in FIGS. 5 through 9 and still other configurations can be used in conjunction with the delivery of a spinal implant device such as an interbody fusion device, artificial disc, nucleus implant, or disc augmentation material, in accordance with the present invention.

FIGS. 10A through 10F illustrate various steps that may be performed in the delivery of a bone-strengthening substance to an intervertebral body. Generally, these steps can be performed by a percutaneous method, or during another (e.g. open) surgical method. Percutaneous methods can be used to particular advantage before or after a surgical implantation of a medical device (e.g. a load bearing interbody device or other spinal implant).

Figure 10A:
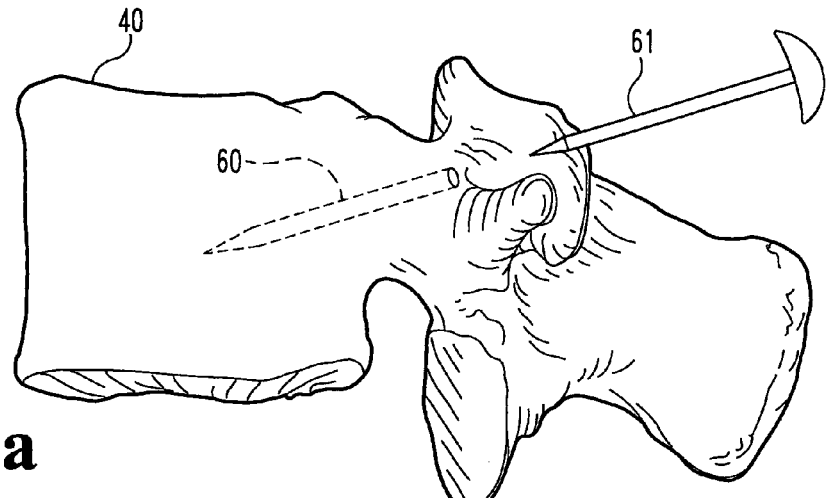
FIGS. 10A through 10F illustrate various steps that may be undertaken in the delivery of a bone-strengthening substance in accordance with the invention.
Figure 10B:
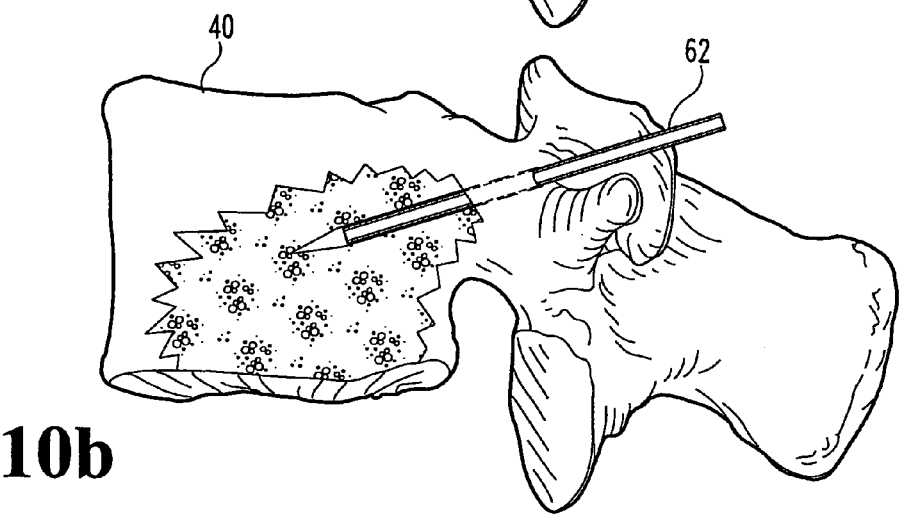
Figure 10C:
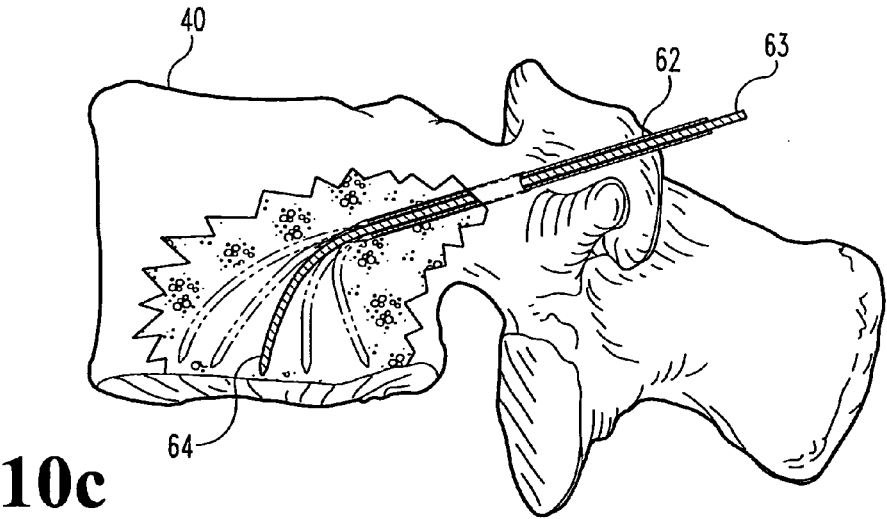
Figure 10D:
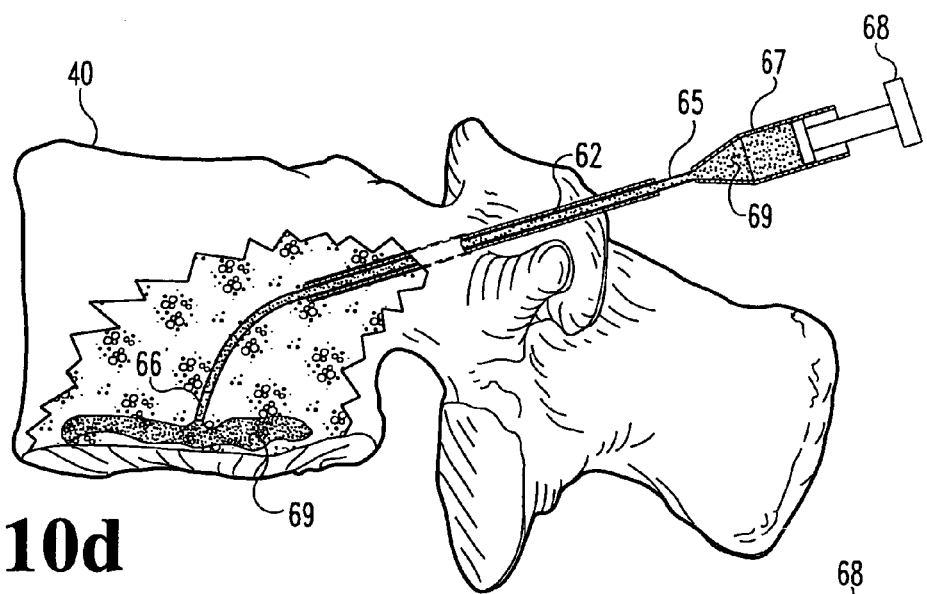

With reference now to FIG. 10A, as a first step, a channel 60 can be created in vertebral body 40 through the pedicle using a suitable bone-penetrating implement such as a trocar needle 61. Thereafter (FIG. 10B) a sheath 62 can be inserted into channel 60 through which various procedures can be implemented. FIG. 10C shows a subsequent step in which a flexible or otherwise steerable needle or drill 63 is positioned through sheath 62 to access regions nearing the endplate of vertebral body 41. As shown, several directional passes of the needle or drill may be used in order to create access to a broader volume of bone. The tip 64 of needled or drill 63 can be designed so as to be steerable, for instance by rotation of needle or drill 63. As illustrated in FIG. 10D, after accessing near the endplate, the needle or drill 63 can be withdrawn, and a delivery device 65 can be inserted through sheath 62. Delivery device 65 can have delivery tip 66, which is curved or otherwise steerable. Delivery device 65 can also include a reservoir 67 and a plunger 68, allowing for the delivery of effective amounts of the osteogenic factor or other bone-strengthening substance 69 out of delivery tip 66.

Figure 10E:
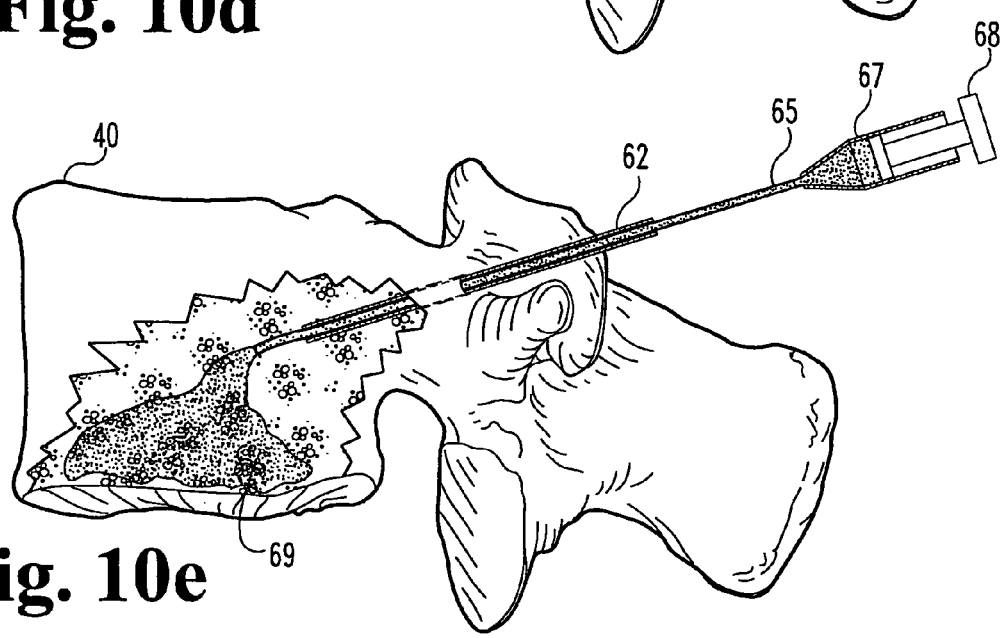
Figure 10F:
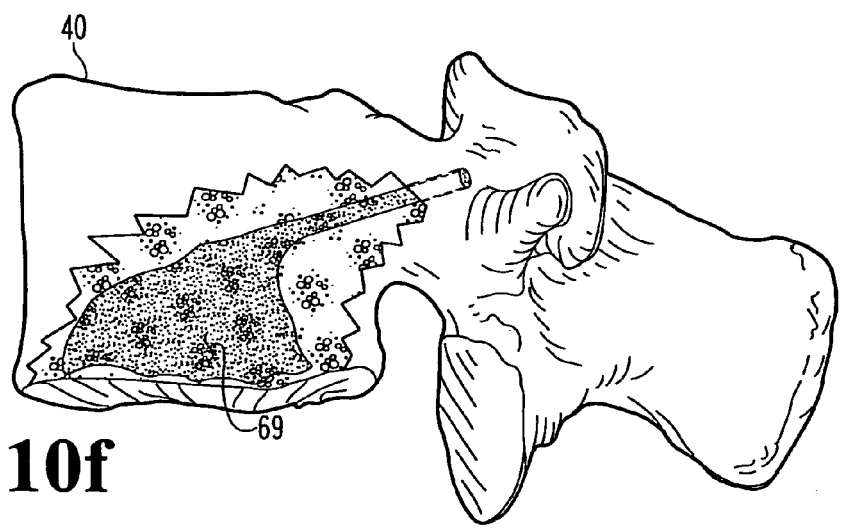

FIG. 10E shows an intermediate stage of the delivery process in which additional amounts of the bone-strengthening substance 69 are delivered as the sheath 62 and the delivery device 65 are withdrawn from the access channel 60. In this manner, the access channel 60 can be backfilled with the substance 69 as the implements are withdrawn. Finally, shown in FIG. 10F is the material 69 occupying a volume overlying an endplate of the vertebral body 40, and also backfilled into the access channel 60.

Figure 11A:
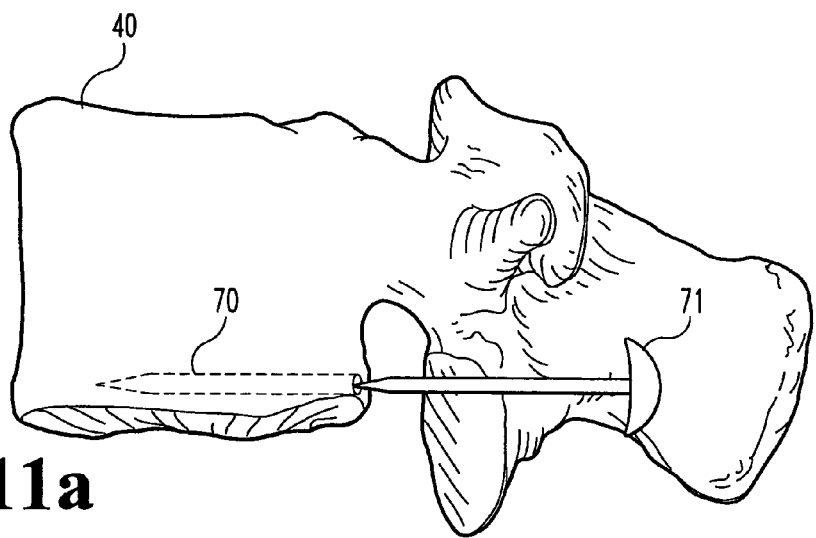
FIGS. 11A through 11C illustrate various steps that may be undertaken in an alternative delivery of a bone-strengthening substance in accordance with the invention.
Figure 11B:
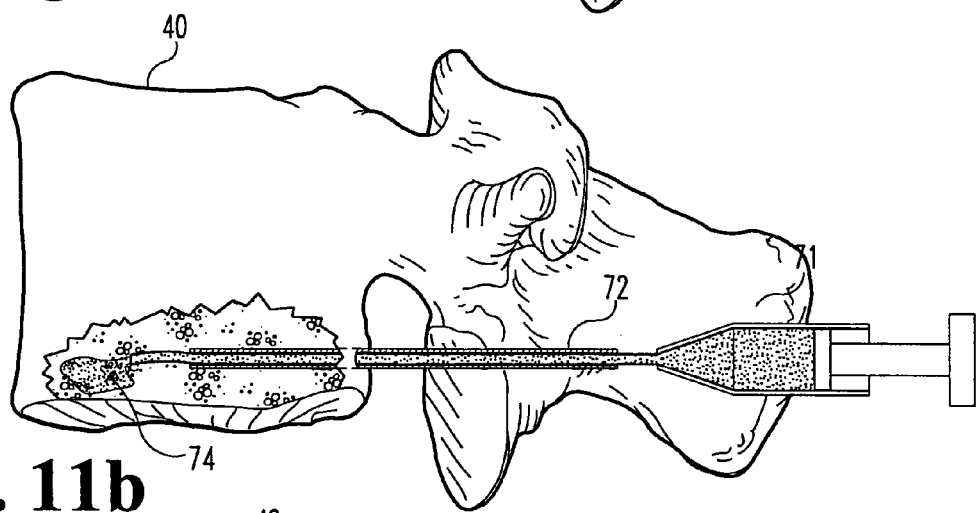
Figure 11C:
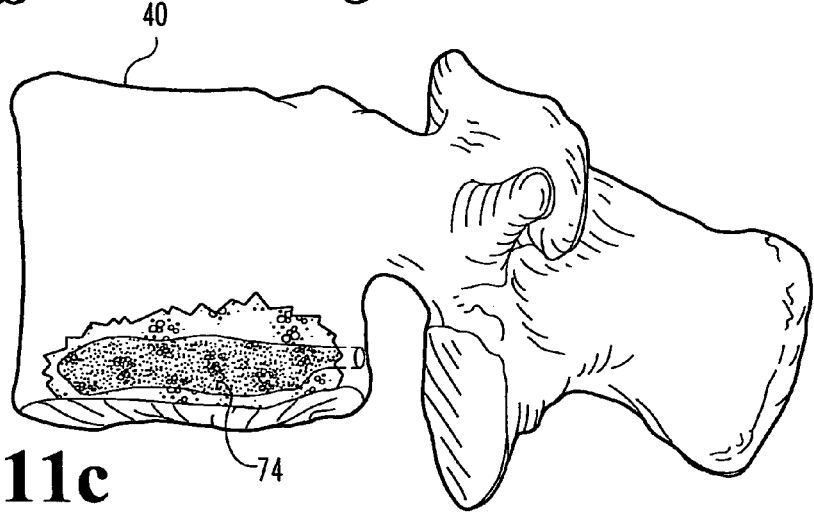

With reference now to FIGS. 11A through 11C, shown are steps in another illustrative access and delivery procedure that can be used to deliver a bone-strengthening material to a volume of bone overlying an endplate of a vertebral body. The steps shown in FIGS. 11A through 11C can be used, for example, in an open surgical procedure in conjunction with the implantation of a medical device such as an interbody device. Referring first to FIG. 11A, an access channel 70 is created in vertebral body 40 just above the endplate using a needle 71 or other bone-penetrating implement. After this access, a sheath 72 is provided into channel 70. A delivery device 73 is then inserted through the lumen of sheath 72 and is used to deliver a bone-strengthening material 74, for example an osteogenic substance, into the vertebral body in a volume overlying the endplate. If desired or needed, a steerable needle or drill can be used to create access to a broader volume of bone, generally as described in conjunction with FIGS. 10A through 10F above. As well, a backfilling procedure can be used to fill the channel 70 as the delivery device 73 and sheath 72 are removed. As shown in FIG. 11C, ultimately, a volume 74 of bone-strengthening material is delivered into vertebral body overlying its endplate. The strengthened volume of bone thus created can, for example, improve resistance to fracture, subsidence, or undesirable remodeling of endplates due to loading created by an interbody implant or material introduced into the adjacent disc space.

Procedures in accordance with the invention can be performed on individuals having normal, healthy bone or also on individuals having diseased or otherwise abnormal bone. For example, procedures of the invention can be performed in patients having decreased bone density. This may result from a disorder such as osteoporosis, osteomalacia, osteotis fibrosa, Paget's disease, bone deficiency, primary or secondary hyperparathyroidism, chronic inflammatory conditions, metastatic bone disease and osteolytic bone disease. When the condition is osteoporosis, the osteoporosis can be due to a number of conditions, e.g., age-related osteoporosis, postmenopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis.

As noted above, certain methods of the invention involve the use of an osteogenic substance to strengthen volumes of bone within spinal vertebrae. The osteogenic substance can be any suitable such substance known in the art. In this regard, the osteogenic substance can include an osteogenic factor incorporated within a suitable pharmaceutically-acceptable carrier.

The osteogenic factor may, for example, be an osteogenic protein such as a bone morphogenic protein (BMP). The bone morphogenic protein (BMP) can be any BMP effective to stimulate the formation of bone. Examples of such BMPs are BMP-2, BMP-4, and BMP-7, more preferably rhBMP-2 or rhBMP-7, most preferably, rhBMP-2. Purified recombinant BMPs are preferred for use in the inventive compositions for their provision of high osteoinductive potentials. BMP gene sequences and methods for producing recombinant and naturally-derived BMPs are known in the art, and for additional information on this subject reference may be made, for instance, to U.S. Pat. Nos. 5,108,753; 5,187,076; 5,366,875; 4,877,864; 5,108,922; 5,116,738; 5,013,649; 5,106,748; and 4,294,753; and International Publication Nos. WO93/00432; WO94/26893; and WO94/26892. The osteoinductive factor may also be LIM mineralization protein (LMP) as described in WO99/06563 (see also genbank accession No. AF095585).

The osteogenic factor will be incorporated into a suitable pharmaceutical formulation and used in an amount which is effective to stimulate the formation of bone within the animal recipient. In certain compositions incorporating osteogenic proteins, the protein will be incorporated in a weight ratio of about 1:100 to about 1:1000 relative to the overall composition, more commonly about 1:100 to about 1:500.

Osteogenic compositions for the invention may also include other osteoinductive substances, including for example demineralized bone matrix (DBM). As is known in the field, DBM can be prepared by acid demineralization of bone and when so prepared contains, among other constituents, the collagen matrix of the bone and acid insoluble proteins. DBM has been shown previously to be mildly osteoinductive by itself and has a favorable porous matrix for the ingrowth of bone. Methods of producing DBM are known in the art and are, therefore not elaborated upon here (see for example U.S. Pat. No. 5,405,390).

The osteogenic composition used in the invention may take a variety of forms. For example, the osteogenic composition may be a relatively simple, non-viscous liquid composition such as an aqueous solution of an osteogenic protein. Alternatively, the osteogenic composition may be a relatively more viscous substance such as a paste or gel. Further, the osteogenic composition may have properties that allow it to increase in viscosity once delivered into the bone tissue. In this fashion, while in a relatively non-viscous state, the osteogenic composition can be delivered into the bony tissue and can penetrate the pores of the bony tissue so as to deliver the osteogenic composition across a relatively large volume from a single point of injection or other delivery. After dispersal through the volume of bony tissue, the osteogenic composition can take on a more viscous or hardened state and thereby hold the osteogenic protein within the delivered volume. Moreover, the relatively viscous, delivered composition may or may not include components that act as a scaffold for the ingrowth of bone.

A wide variety of suitable carriers may be incorporated into osteogenic compositions of the invention. In certain forms, the carrier will be biologically resorbable and will contribute to providing a relatively viscous form of composition allowing its implantation and retention at a site for bone ingrowth. In this regard, carriers may include resorbable macromolecules from biological or synthetic origins, including for example gelatin, hyaluronic acid, carboxymethylcellulose, collagen, peptides, and the like. Additional carrier substances includes glycols such as polyethylene glycol, chitosan, elastin, albumin, fibrin, keratin, lecithin, cellulose-based materials, polyethylene oxide, polyvinyl alcohol, calcium sulfate, calcium phosphate (including for example hydroxyapatite and/or tricalcium phosphates generally), calcium carbonate, or combinations thereof.

In certain forms of the invention, an osteogenic composition is provided and used that includes a relatively quickly resorbable material along with a relatively slowly resorbable material. For example, relatively rapid resorbing materials include those identified above as carrier materials. Relatively slow carrier materials may include calcium-containing solid materials in particulate form, such as powders. The particle size will be sufficiently small to retain the flowable and injectable character of the osteogenic composition. To this end, in certain embodiments the average particle size ranges from about 1 nanometer to about 100 micrometers. Examples of suitable calcium-containing materials include hydroxylapatite, calcium phosphate, tricalcium phosphate, biphasic calcium phosphate, calcium carbonate, bioactive glasses, or combinations thereof. These compositions may be provided initially in a powder form, including a powder mixture of the rapid and slow resorbing materials. This powder mixture can then be combined with a liquid such as an aqueous solution to form a flowable composition, desirably an injectable composition. Still further, in certain forms, this flowable composition increases in viscosity after delivery, to harden and hold the osteogenic substance within the delivered volume.

In accordance with the invention, the osteogenic composition can be delivered to any suitable bony tissue volume within one or more vertebrae of the recipient. The bony tissue volume may be constituted by healthy bony tissue, or by diseased, damaged, or otherwise weakened bony tissue. Illustratively, the bony tissue may be characterized as having a decreased bone density due to osteoporosis in the recipient or other causes. As well, the bony tissue may be at or near the site of a lesion which damaged the tissue, or other injured tissue. In cases wherein a medical device is to be inserted within the interbody space between adjacent vertebra, one or more of the adjacent vertebra may receive delivery of the osteogenic composition in a volume generally lying internally of the endplates of the vertebrae, as depicted in certain of the Figures. On the other hand, where connectors or other devices are to be attached to or inserted through horizontal or external surface of a vertebra, the volume of bony tissue in which the connector is to be received can be treated with the osteogenic substance, as well as any adjacent volumes that will receive tensile, shear, compression, or other forces from the connector or from plates, rods, or other elements associated with the connector.

In certain embodiments of the invention, a bone-strengthening substance, which may or may not include an osteogenic material, can be used. For example, a bone cement formulation lacking or containing an osteogenic portein may be used. In this regard, any suitable bone cement material can be incorporated into such formulations. In certain forms, the bone cement material will include a solid finely divided powdery or granular polymer component, and a liquid reactive or polymerizable monomer component that also serves as a solvent or swelling agent for the polymer component. The polymer and monomer components can be based on the acrylic, e.g., (meth)acrylate system, however, other polymeric systems can also be used. A common polymer component included in bone cement is PMMA (polymethylmethacrylate).

More generally, in certain embodiments, the polymer component of the composition can be any methyl acrylate or methyl methacrylate polymer (together herein encompassed by the abbreviated expression "methyl(meth)acrylate" polymers wherein "(meth)" denotes the optional presence of the methyl group) such as methyl(meth)acrylate homopolymers and copolymers of methyl(meth)acrylate with alpha, beta-ethylenically unsaturated compounds such as vinyl acetate, alkyl (e.g. $C_2$-$C_6$) (meth)acrylates and multi-functional acrylic monomers such as alkylene dimethacrylate and alkylene diacrylates and triacrylates. These polymers commonly have a molecular weight between about 500,000 and about 2,000,000.

The reactive monomer component can be methyl acrylate or methyl methacrylate although the $C_2$-$C_4$ alkyl(meth)acrylates, such as ethyl(meth)acrylate, propyl(meth)acrylate or (n-, or iso-) butyl(meth) acrylate, can also be used.

Generally, such bone cement materials are well known and commercially available. They are usually provided as finely divided polymer and liquid monomer, and are characterized as being self-polymerizable substances which are mixed, together with a polymerization catalyst, such as dibenzoyl peroxide, and polymerization accelerator, such as dimethyl-p-toluidine, immediately prior to the operation to form a viscous liquid or pasty mass. The pasty mass is introduced into the appropriate site and will harden in situ (via an exothermic reaction) within a few minutes.

The osteogenic composition or other bone-reinforcing substance (e.g. bone cement) can be delivered to the volume of bony tissue using any suitable method. These include, for example, delivery through a needle or other cannulated device. In this regard, certain devices are known for the delivery of bone cements or other formulations into vertebral bodies. Illustrative such devices are disclosed in U.S. Pat. Nos. 6,375,659, 6,348,055 and 6,582,439. Such devices may be used in methods of the present invention.

In the delivery of the osteogenic composition or other bone-strengthening material, a single injection may be used, or a multiple injections may be used at varied sites within the volume in which strengthened bone is desired. As well, needles having adaptations for delivery within larger volumes, such as having a plurality of holes or orifices in the end and/or side areas of the needle, can be used. Any suitable method for delivery of the osteogenic or other bone-strengthening composition into a functional volume of bony tissue is contemplated as within the present invention.

As well, to assist in the identification of the volume in which the composition is delivered, the composition can be rendered radiopaque by the addition of suitable substances, for examples those containing barium, tungsten, or the like. Further in this regard, the procedures for delivering the osteogenic or other bone-strengthening substance can be performed and guided under conventional imaging techniques such as fluoroscopy. As well, conventional techniques can be used to identify patients and/or bone regions having a need for reinforcement. For example, in the case of decreased bone density, this can be detected utilizing methods well known in the art, e.g., bone density scans, radiographic imaging, medical history, and the like.

Additional aspects of the invention relate to surgical kits that are useful in the performance of methods such as those described herein. Thus, in certain embodiments, the invention provides surgical kits that include a medical device configured for spinal implant, a bone-strengthening substance such as an osteogenic substance, and a delivery device effective to deliver the osteogenic substance into a volume of bone tissue within the vertebra of a patient in which the medical device is to be implanted. The medical device, delivery device, and bone-strengthening substance may, as examples, include any combination of those elements described herein.

While various preferred embodiments of the invention have been described in detail above, the same is to be considered illustrative in nature. All modifications and additions as would occur to one of ordinary skill in the field to which this invention pertains are contemplated as being a part of this invention and are desired to be protected. In addition, all publications cited herein are indicative of the level of ordinary skill in the art, and are hereby incorporated by reference in their entirety as if each had been individually incorporated by reference where cited and fully set forth.

What is claimed is:

1. A method for implanting a medical device in the spine of a patient, comprising:
   accessing the spine of a patient having a healthy vertebra and an unfractured vertebra with internal bone tissue of decreased density creating a risk of fracture;
   implanting a medical device in the spine of the patient in the healthy vertebra and adjacent to the unfractured vertebra, wherein the medical device causes loads to be imparted to the internal bone tissue of the vertebra and to the healthy vertebra of the patient and the medical device is a fusion device; and
   delivering into an internal volume of the internal bone tissue of the vertebra and into the healthy vertebra an osteogenic substance effective to strengthen the internal volume of the bone tissue to reduce the risk of fracture and to strengthen the healthy vertebra via a delivery device inserted into said internal volume of the bone tissue and into the healthy vertebra, wherein the osteogenic substance has a flowable condition during delivery, and a hardened condition after delivery, and the osteogenic substance is a bone morphogenic protein.

2. The method of claim 1, wherein said implanting and delivering are performed during a single surgical procedure.

3. The method of claim 1, wherein said implanting and delivering are performed in separate surgical procedure.

4. The method of claim 3, wherein said implanting is performed prior to said delivering.

5. The method of claim 3, wherein said implanting is performed after said delivering.

6. The method of claim 1, wherein:
   said implanting is conducted after providing sufficient time for said internal volume of bone tissue to strengthen.

7. The method of claim 1, wherein said delivery device is cannulated.

8. The method of claim 1, further comprising:
   inserting said delivery device into said internal volume of bone tissue prior to said delivering; and withdrawing said delivery device after said delivering.

9. The method of claim 8, wherein said delivery device is cannulated.

10. A method for implanting a medical device in the spine of a patient, comprising:
    accessing the spine of a patient having an unfractured volume of bone and a healthy vertebra, said volume of bone having decreased density creating a risk of fracture;
    implanting a medical device in the spine of the patient in the healthy vertebra, wherein the medical device imparts loads indirectly to said volume of bone spaced from said medical device and the healthy vertebra and the medical device is a fusion device; and
    delivering a bone-strengthening substance to said volume of bone and into the healthy vertebra via a delivery device inserted into said volume of bone to reduce the risk of fracture and into the healthy vertebra to strengthen the healthy vertebra, wherein the bone-strengthening substance has a flowable condition during delivery and a hardened condition after delivery, and the bone strengthening substance comprises a bone morphogenic protein.

11. The method of claim 10, wherein the medical device is implanted in healthy adjacent vertebral bodies of the spine, and wherein said volume of bone is adjacent to a vertebral endplate of at least one of said vertebral bodies.

12. The method of claim 10, wherein said delivery device is cannulated.

13. The method of claim 10, further comprising:
    inserting said delivery device into said volume of bone prior to said delivering;
    and withdrawing said delivery device after said delivering.

14. The method of claim 13, wherein said delivery device is cannulated.

* * * * *